United States Patent [19]  
Regnier et al.

[11] 4,267,178  
[45] May 12, 1981

[54] DISUBSTITUTED PIPERAZINES

[75] Inventors: Gilbert Regnier, Chatenay Malabry; Michel Laubie, Vaucresson; Jean-Claude Poignant, Bures sur Yvette, all of France

[73] Assignee: Science Union et Cie, Societe Francaise de Recherche Med., Surësnes, France

[21] Appl. No.: 14,876

[22] Filed: Feb. 26, 1979

[30] Foreign Application Priority Data

Mar. 3, 1978 [GB] United Kingdom ............... 8530/78

[51] Int. Cl.³ .................. A61K 31/36; A61K 31/335; C07C 405/14
[52] U.S. Cl. .................................. 424/250; 424/251; 544/295; 544/364; 544/369; 544/367
[58] Field of Search ............... 544/295, 360, 369, 377, 544/364, 367; 424/250, 251

[56] References Cited  
U.S. PATENT DOCUMENTS 2,543,972   3/1951   Hultquist et al. ................ 544/360

Primary Examiner—Jose Tovar  
Attorney, Agent, or Firm—Omri M. Behr

[57] ABSTRACT

Disubstituted piperazines of the formula

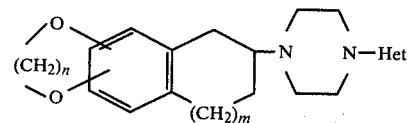

in which
 n is 1 or 2,
 m is 0 or 1, and
 Het is pyridyl, pyrimidinyl, pyrazinyl, thiazolyl or thiadiazolyl each optionally substituted by one or more alkyl having from 1 to 5 carbon atoms inclusive.

These compounds and their physiologically tolerable acid addition salts thereof may be used as medicines especially in the treatment of hypertension.

8 Claims, No Drawings

DISUBSTITUTED PIPERAZINES

The present invention provides disubstituted piperazines of the formula:

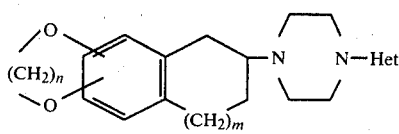

in which:

n is selected from 1 to 2, m is selected from 0 and 1, and

Het is selected from the group consisting of pyridyl, pyrimidinyl, pyrazinyl, thiazolyl and thiadiazolyl radicals and each of these radicals mono- and poly-substituted by alkyl radicals having from 1 to 5 carbon atoms inclusive As alkyl radicals there may be mentioned, for example, methyl, ethyl, propyl, butyl and pentyl radicals.

The present invention also provides acid addition salts of the compounds of the general formula I.

The acid addition salts are preferably physiologically tolerable acid addition salts.

Due to their phamacological properties the preferred compounds are the compounds of the formula I in which n and m are as defined above and Het is selected from the groups consisting of pyridyl, pyrimidyl, and thiazolyl radicals and each of these radicals mono- and poly-substituted by alkyl radicals having from 1 to 5 carbon atoms inclusive and physiologically tolerable acid addition salts thereof.

The present invention also provides a process for preparing compounds of the general formula I which comprises condensing a N-monosubstituted piperazine of the general formula:

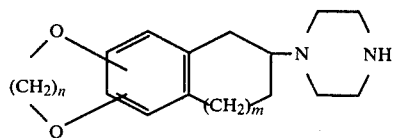

wherein n and m have the meanings given above, with a halo compound of the general formula Het—Hal    III wherein Het has the meaning given above and Hal represents a chlorine or a bromine atom.

Such a process is advantageously carried out by reacting the compounds II and III in solution in an aromatic hydrocarbon having a high boiling point such for example as toluene or xylene, in an aliphatic amide such for example as dimethylformamide or dimethylacetamide, or in an alcohol having a high boiling point such for example as butanol or pentanol. It is advantageous to carry out the process at a temperature within the range of from 110° to 150° C., in presence of an acceptor for the hydrogen halide formed during the reaction. As acceptors, there may be mentioned, for example, alkali metal salts of carbonic acid, such for example as sodium or potassium carbonate, tertiary amines such for example as triethylamine, or an excess of the monosubstituted piperazine of the formula II, the excess acting as the acid acceptor.

The present invention also provides a process for preparing compounds of the general formula I which comprises reacting a keto compound of the general formula

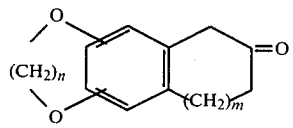

wherein n and m have the meanings given above, with a N-monosubstituted piperazine of the general formula:

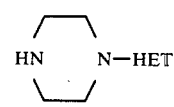

wherein Het has the meaning given above, then hydrogenizing the so-obtained enamine of the general formula:

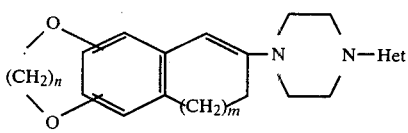

wherein n, m and Het have the meanings given above, either with hydrogen in the presence of a catalyst, or with a borohydride or a cyanoborohydride of the formula $BH_3XM$ wherein X represents a hydrogen atom or a cyano radical, and M represents an alkaline metal such for example sodium or potassium.

The reaction of compounds IV and V is advantageously carried out azeotropically in an aromatic hydrocarbon having a high boiling point such for example as toluene or xylene, or in a water immixible alcohol such for example as pentanol, in the presence of a catalyst which may be for example acetic acid or paratoluene sulfonic acid.

The hydrogenation of the enamine VI with hydrogen is advantageous carried out in a solvent which may be for example an alcohol having a low molecular weight such for example as methanol or ethanol, ethyl acetate, dimethyl formamide, or methyl cellosolve, at a temperature ranging from 25° to 80° C., under a hydrogen pressure of from 2 to 10 atmospheres in the presence of a catalyst containing group VIII metal such as platinum or palladium. As suitable catalyst, there may be mentioned for example Pt $O_2$ or palladium-on charcoal containing from 5 to 10% Pd.

The hydrogenation of the enamine VI with a compound $BH_3XM$, X and M being as defined above, is advantageously carried out in the presence of a halogen hydride in a suitable solvent which may be an alcohol having a low molecular weight preferably methanol or an ether preferably tetrahydrofuran. When X is a cyano radical, the reduction is performed according to the method described by R. Borch and al, J. am. Chem. soc. 93, 2897 (1971), with the protonic form of the enamine, with one equivalent of the halogen hydride or acetic acid in solution in the solvent used for the reduction. Such a reaction is advantageous carried out by treating at room temperature one equivalent of the enamine, in solution in an appropriate solvent such for example as tetrahydrofuran, methanol or a mixture tetrahydrofuran and methanol, with one equivalent of halogen hydride preferably hydrogen chloride or acetic acid in solution in the same solvent, then adding one equivalent of the chosen borohydride in solution in the same solvent.

The starting materials used for these processes are known compounds, or they may prepared according to methods described in the literature for preparing similar compounds as mentioned in the following examples.

The compounds of the general formula I are weak bases which may be converted by treatment with acids into acid addition salts. As acids which may be used for the formation of these addition salts, there may be mentioned for example, in the mineral series: hydrochloric, hydrobromic, sulphuric and phosphoric acids; and in the organic series: acetic, propionic, maleic, fumaric, tartaric, citric, oxalic, benzoic, methane-sulphonic and isethionic acids.

The compounds of the formula I may be purified by physical methods, for example, crystallization or chromatography, or by chemical methods, for example by formation of an addition salt followed by crystallization of the latter and decomposition thereof with an alkaline agent.

The compounds of the general formula I and physiologically tolerable acid addition salts thereof possess valuable pharmacological and therapeutic properties especially anti-hypertensive, activating of local blood flow by a direct action on peripheral resistances and also central activating properties more particularly on dopaminergic areas. They may be used therefore, as medicines especially in the treatment of arterial hypertension of different origins, circulatory deficits in cardiac, cerebral and peripheral areas, and extrapyramidal motor disorders especially Parkinsonian disorders.

Their toxicity is low and then LD 50 determined in mice is higher than 100 mg/kg per intraperitoneal route or higher than 1000 mg/kg per oral route.

The anti-hypertensive activity of the compounds of the invention was studied in the dog anesthetized with Membutal at a dose of 30 mg/kg. A catheter, placed in the aorta, in joined to a cell of pressure STATHAM, and the blood pressure is registered together with the cardiac rhythm. The compounds of the invention administered at a dose of 2 mg/kg per intravenous route give a decrease of blood pressure down to 50% while the cardiac rhythm is either unchanged or slightly decreased.

The activity of the compounds of the invention on peripheral blood flow, was determined in the dog by the measure of the femoral blood flow by the means of a captor placed on the femoral artery and linked to a flowmeter MICRON. For a dose of 2 mg/kg I.V. of the compounds of the invention, the increase of the femoral output may be up to 30%.

The effect of the compounds of the invention on the carotid occlusion was determined in the dog by clamping the two carotids for 30 seconds and recording the modifications of blood pressure and cardiac rhythm. When the compounds of the invention are administered at doses which gradually reach 2 mg/kg I.V., there was obtained a decrease of up to 75% of the effects of carotid occlusion on the blood pressure.

The scores of CNS stimulation of stereotypy were determined, on the rats, according to the method of Quinton and Halliwell, Nature 200, n° 4902, p. 178 (1963). The scores for 3 hours raised up to 176 with a dose of 80 mg/kg I.P. of the compounds of the invention.

The determination of rotations on the rats was performed according to the method of Ungerstedt U., European Journal of Pharmacology, 5, (1968)-107–110. When administered at a dose of 25 mg/kg by subcutaneous route, the compounds of the invention give up to 143 rotations for 45 minutes.

The present invention therefore provides a pharmaceutical composition comprising as active ingredient a compound of the general formula I or a physiologically tolerable acid addition salt thereof, in admixture or conjunction with a pharmaceutically suitable carrier, such for example as distilled water, glucose, lactose, starch, talc, magnesium stearate, ethyl cellulose or cocoa butter.

The pharmaceutical compositions of the present invention are advantageously in unit dosage form, and may contain from 1 to 300 mg of the active ingredient.

These pharmacological compositions may be in form of tablets, dragees, capsules, suppositories or injectable or drinkable solutions and may be administered by oral, rectal or parenteral route at dose of 1 to 300 mg, 1 to 4 times a day.

The following examples illustrate the invention, the melting points being determined in a capillary tube, unless otherwise stated.

EXAMPLE 1

1-(6,7-methylenedioxy-1,2,3,4-tetrahydro-2-naphthyl)-4-(2-pyrimidinyl) piperazine.

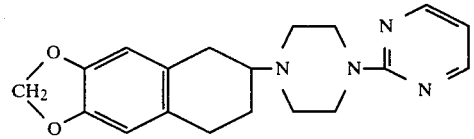

First method:

A solution of 2.6 g of 1-(6,7-methylenedioxy-1,2,3,4-tetrahydro-2-naphthyl) piperazine, 1.5 g of 2-chloropyrimidine and 1.4 g of potassium carbonate in 50 ml of anhydrous dimethylformamide, was heated at 130° C. for 3 hours. Then the reactional mixture was cooled, the so-formed salt was filtered out and the solvent was evaporated under reduced pressure. The so-obtained residue was taken up with 30 ml of a normal solution of methanesulphonic acid and 15 ml of chloroform. The mixture was decanted off, and the acid solution was alkalized with potassium carbonate. The base was extracted with chloroform. The solution was dried and the solvent was evaporated. There were obtained 3 g of crude product which recrystallized in 40 ml of ethanol gave 2 g of 1-(6,7-methylenedioxy-1,2,3,4-tetrahydro-2-naphthyl)-4-(2pyrimidinyl) piperazine, beige crystals melting at 134°–135° C. The corresponding monomethanesulfonate melts at 218°–225° C.

The starting 1-(6,7-methylenedioxy-1,2,3,4-tetrahydro-2-naphthyl) piperazine, is an oil which was obtained by alkaline hydrolysis of the corresponding carbethoxy derivative, itself prepared according to the below second method, from 1-(6,7-methylenedioxy-3,4-dihydro-2-naphthyl)-4-carbethoxy piperazine, melting at 120° C.
Second method:

A solution of 3.8 g of 6,7-methylenedioxy-2-tetralone and 3.3 g of 1-(2-pyrimidinyl) piperazine in 100 ml of anhydrous toluene was boiled for 30 minutes in the presence of 100 mg of p.toluenesulphonic acid, in a Dean and Stark apparatus. When the theoretical quantity of water was collected, the solution was cooled and washed with twice 20 ml of water. The solution was then decanted off, and the solvent was evaporated under reduced pressure. The residue was taken up with petroleum ether, and there were obtained 6.4 g of 1-(6,7-methylenedioxy-3,4-dihydro-2-naphthyl)-4-(2-pyrimidinyl) piperazine, beige crystals melting at 155°-160° C.

6 g of the so-obtained enamine were dissolved in 500 ml of methylcellosolve at 50° C., and the so-obtained solution was hydrogenated under a hydrogen pressure of 5 atmospheres in the presence of 600 mg of Pt $O_2$, at room temperature. 24 hours later the theoretical amount of hydrogen was absorbed. The catalyst was filtered off and the solvent was evaporated under reduced pressure. The residue was recrystallised in 50 ml of ethanol and there were obtained 2.7 g of 1-(6,7-methylenedioxy-1,2,3,4-tetrahydro-2-naphthyl)-4-(2-pyrimidinyl) piperazine, beige crystals melting at 134°-135° C.

The reduction of 1-(6,7-methylenedioxy-3,4-dihydro-2-naphthyl)-4-(2-pyrimidinyl) piperazine, was also performed as follows:

There were added 2 ml of a solution 5 N of HCl in tetrahydrofuran to a solution of 3.35 g of 1-(6,7-methylenedioxy-3,4-dihydro-2-naphthyl)-4-(2-pyrimidinyl) piperazine previously obtained, in 100 ml of anhydrous tetrahydrofuran. The hydrochloride of the enamine precipitated, and there were added, to the so-obtained suspension, 10 ml of a normal solution of sodium cyanoborohydride in tetrahydrofuran. The precipitate was then immediately dissolved and the solution was decolourised. 30 minutes later, the solvent was evaporated off and the residue was taken up with a normal sodium hydroxide solution, then extracted with chloroform. The chloroformic solution was then evaporated under reduced pressure and the viscous residue was taken up with 30 ml of anhydrous ethanol. The product crystallized and there were obtained 2.1 g of 1-(6,7-methylenedioxy-1,2,3,4-tetrahydro-2-naphthyl)-4-(2-pyrimidinyl) piperazine, beige crystals melting at 134°-135° C. The corresponding monomethanesulfonate melts at 218°-225° C.

The starting 6,7-methylenedioxy-2-tetralone was prepared according to the method of R. DRAN and T. PRANGE, Bull. Soc. Chim. (1967), 4469.

EXAMPLES 2 TO 22:

The following compounds were prepared according to the processes described in example 1:

(2) 1-(6,7-methylenedioxy-1,2,3,4-tetrahydro-2-naphthyl)-4-(2-pyridyl) piperazine, M.P. (Kofler) 144° C. (acetonitrile), starting from:
1-(6,7-methylenedioxy-1,2,3,4-tetrahydro-2-naphthyl) piperazine and 2-chloropyridine, or
6,7-methylenedioxy-2-tetralone and 1-(2-pyridyl) piperazine.

(3) 1-(6,7-methylenedioxy-1,2,3,4-tetrahydro-2-naphthyl)-4-(2-thiazolyl) piperazine, M.P. of its dihydrochloride 250°-255° C. (anhydrous ethanol) starting from:
1-(6,7-methylenedioxy-1,2,3,4-tetrahydro-2-naphthyl) piperazine and 2-chlorothiazole, or
6,7-methylenedioxy-2-tetralone and 1-(2-thiazolyl) piperazine.

(4) 1-(6,7-methylenedioxy-1,2,3,4-tetrahydro-2-naphthyl)-4-(1,3,4-thiadiazol-2-yl) piperazine, M.P. 160°-161° C. (acetonitrile), starting from:
1-(6,7-methylenedioxy-1,2,3,4-tetrahydro-2-naphthyl) piperazine and 2-chloro-1,3,4-thiadiazole, or
6,7-methylenedioxy-2-tetralone and 1-(1,3,4-thiadiazol-2-yl) piperazine.

(5) 1-(6,7-methylenedioxy-1,2,3,4-tetrahydro-2-naphthyl)-4-(2-pyrazinyl) piperazine, M.P. 120°-122° C. (acetonitrile), starting from:
1-(6,7-methylenedioxy-1,2,3,4-tetrahydro-2-naphthyl) piperazine and 2-chloropyrazine, or
6,7-methylenedioxy-2-tetralone and 1-(2-pyrazinyl) piperazine.

(6) 1-(5,6-methylenedioxy-1,2,3,4-tetrahydro-2-naphthyl)-4-(2-pyrimidinyl) piperazine, starting from:
1-(5,6-methylenedioxy-1,2,3,4-tetrahydro-2-naphthyl) piperazine and 2-chloropyrimidine, or
5,6-methylenedioxy-2-tetralone, prepared by analogy with the method of J. CANNON and al, J. Med. Chem. 20, 1111, (1977), and 1-(2-pyrimidinyl) piperazine.

(7) 1-(5,6-methylenedioxy-1,2,3,4-tetrahydro-2-naphthyl)-4-(2-pyridyl) piperazine, starting from:
1-(5,6-methylenedioxy-1,2,3,4-tetrahydro-2-naphthyl) piperazine and 2-chloropyridine, or
5,6-methylenedioxy-2-tetralone and 1-(2-pyridyl) piperazine.

(8) 1-(5,6-methylenedioxy-1,2,3,4-tetrahydro-2-naphthyl)-4-(2-thiazolyl) piperazine, starting from:
1-(5,6-methylenedioxy-1,2,3,4-tetrahydro-2-naphthyl) piperazine and 2-chlorothiazole, or
5,6-methylenedioxy-2-tetralone and 1-(2-thiazolyl) piperazine.

(9) 1-(5,6-methylenedioxy-1,2,3,4-tetrahydro-2-naphthyl)-4-(1,3,4-thiadiazol-2-yl) piperazine, starting from:
1-(5,6-methylenedioxy-1,2,3,4-tetrahydro-2-naphthyl) piperazine and 2-chloro-1,3,4-thiadiazole, or
5,6-methylenedioxy-2-tetralone, and 1-(1,3,4-thiadiazol-2-yl) piperazine.

(10) 1-(6,7-ethylenedioxy-1,2,3,4-tetrahydro-2-naphthyl)-4-(2-pyrimidinyl) piperazine, starting from:
1-(6,7-ethylenedioxy-1,2,3,4-tetrahydro-2-naphthyl) piperazine and 2-chloropyrimidine, or
6,7-ethylenedioxy-2-tetralone, and 1-(2-pyrimidinyl) piperazine.

(11) 1-(6,7-ethylenedioxy-1,2,3,4-tetrahydro-2-naphthyl)-4-(2-thiazolyl) piperazine, starting from:
1-(6,7-ethylenedioxy-1,2,3,4-tetrahydro-2-naphthyl) piperazine and -2-chlorothiazole, or
6,7-ethylenedioxy-2-tetralone, and 1-(2-thiazolyl) piperazine.

(12) 1-(6,7-ethylenedioxy-1,2,3,4-tetrahydro-2-naphthyl)-4-(1,3,4-thiadiazol-2-yl) piperazine, starting from:
1-(6,7-ethylenedioxy-1,2,3,4-tetrahydro-2-naphthyl) piperazine and 2-chloro-1,3,4-thiadiazole, or
6,7-ethylenedioxy-2-tetralone, and 1-(1,3,4-thiadiazol-2-yl) piperazine.

(13) 1-(5,6-methylenedioxy-2-indanyl)-4-(2-pyrimidinyl) piperazine, M.P. of its monomethanesulfonate: 265°-270° C. (methanol) starting from:

1-(5,6-methylenedioxy-2-indanyl) piperazine, and 2-chloropyrimidine, or 5,6-methylenedioxy-2-indanone, itself prepared according to the method of R. DRAN and T. PRANGE, Bull. Soc. Chim. (1969), 1244, and 1-(2-pyrimidinyl) piperazine.

(14) 1-(5,6-methylenedioxy-2-indanyl)-4-(2-thiazolyl) piperazine, M.P. of its monomethanesulfonate (Kofler) 265° C. (anhydrous methanol), starting from:

1-(5,6-methylenedioxy-2-indanyl) piperazine, and 2-chlorothiazole, or 5,6-methylenedioxy-2-indanone, and 1-(2-thiazolyl) piperazine.

(15) 1-(5,6-methylenedioxy-2-indanyl)-4-(1,3,4-thiadiazol-2-yl) piperazine, M.P. of its monomethanesulfonate: 247°–249° C., (anhydrous methanol), starting from:

1-(5,6-methylenedioxy-2-indanyl) piperazine, and 2-chloro-1,3,4-thiadiazole, or 5,6-methylenedioxy-2-indanone, and 1-(1,3,4-thiadiazol-2-yl) piperazine.

(16) 1-(4,5-methylenedioxy-2-indanyl)-4-(2-pyrimidinyl) piperazine, starting from:

1-(4,5-methylenedioxy-2-indanyl) piperazine, and 2-chloropyrimidine, or 4,5-methylenedioxy-2-indanone, itself prepared according to the method of R. DRAN and T. PRANGE, Bull. Soc. Chim. (1969) 1244, and 1-(2-pyrimidinyl) piperazine.

(17) 1-(4,5-methylenedioxy-2-indanyl)-4-(2-thiazolyl) piperazine, starting from:

1-(4,5-methylenedioxy-2-indanyl) piperazine, and 2-chlorothiazole, or 4,5-methylenedioxy-2-indanone, and 1-(2-thiazolyl) piperazine.

(18) 1-(4,5-methylenedioxy-2-indanyl)-4-(1,3,4-thiadiazol-2-yl) piperazine, starting from:

1-(4,5-methylenedioxy-2-indanyl) piperazine, and 2-chloro-1,3,4-thiadiazole, or 4,5-methylenedioxy-2-indanone, and 1-(1,3,4-thiadiazol-2-yl) piperazine.

(19) 1-(5,6-methylenedioxy-2-indanyl)-4-(2-pyrazinyl) piperazine, M.P. of its monomethanesulfonate (Kofler)>260° C. (anhydrous methanol), starting from:

1-(5,6-methylenedioxy-2-indanyl) piperazine and 2-chloropyrazine, or 5,6-methylenedioxy-2-indanone and 1-(2-pyrazinyl) piperazine.

(20) 1-(5,6-methylenedioxy-2-indanyl)-4-(2-pyridyl) piperazine, M.P. of its monomethanesulfonate (Kofler): 254° C. (anhydrous methanol) starting from:

1-(5,6-methylenedioxy-2-indanyl) piperazine and 2-chloropyridine, or 5,6-methylenedioxy-2-indanone and 1-(2-pyridyl) piperazine.

(21) 1-(6,7-methylenedioxy-1,2,3,4-tetrahydro-2-naphthyl)-4-(4-methyl-2-pyrimidinyl) piperazine, starting from:

1-(6,7-methylenedioxy-1,2,3,4-tetrahydro-2-naphthyl) piperazine and 4-methyl-2-chloropyrimidine, or 6,7-methylenedioxy-2-tetralone and 1-(4-methyl-2-pyrimidinyl) piperazine.

(22) 1-(6,7-methylenedioxy-1,2,3,4-tetrahydro-2-naphthyl)-4-(6-methyl-2-pyridyl) piperazine, starting from:

1-(6,7-methylenedioxy-1,2,3,4-tetrahydro-2-naphthyl) piperazine and 6-methyl-2-chloropyridine, or 6,7-methylenedioxy-2-tetralone and 1-(6-methyl-2-pyridyl) piperazine.

We claim:

1. A compound selected from the group consisting of: disubstituted piperazines of the formula:

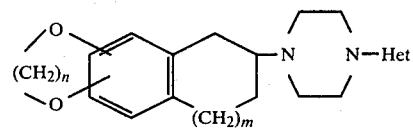

in which:
n is selected from 1 and 2;
m is selected from 0 and 1, and
Het is selected from the group consisting of pyridyl, pyrimidinyl, pyrazinyl, thiazolyl and thiadiazolyl and each of these radicals mono- and poly-substituted by alkyl having from 1 to 5 carbon atoms inclusive; and, physiologically tolerable acid addition salts thereof.

2. Compounds of claim 1, of the formula I, in which n and m have the meanings given in claim 1 and Het is selected from the group consisting of pyridyl, pyrimidinyl and thiazolyl and each of these radicals mono- and poly-substituted by alkyl having from 1 to 5 carbon atoms inclusive, and physiologically tolerable acid addition salts thereof.

3. A compound of claim 1 which is 1-(6,7-methylenedioxy-1,2,3,4-tetrahydro-2-naphtyl)-4-(2-pyrimidinyl) piperazine, and its monomethanesulfonate.

4. A compound of claim 1 which is 1-(6,7-methylenedioxy-1,2,3,4-tetrahydro-2-naphthyl)-4-(2-pyridyl) piperazine.

5. A compound of claim 1 which is 1-(6,7-methylene dioxy-1,2,3,4-tetrahydro-2-naphthyl)-4-(2-thiazolyl) piperazine, and its dihydrochloride.

6. A compound of claim 1 is 1-(5,6-methylenedioxy-2-indanyl)-4-(2-pyridyl) piperazine, and its monomethane sulfonate.

7. An antihypertensive pharmaceutical composition containing as active ingredient a compound of claim 1 in an amount of 1 to 300 mg, together with a suitable pharmaceutical carrier.

8. A method for treating a living animal body afflicted with hypertension, comprising the step of administering an amount of a compound of claim 1 which is effective for the alleviation of the said condition.

* * * * *